US00PP34393P2

(12) United States Plant Patent
Nishikawa

(10) Patent No.: US PP34,393 P2
(45) Date of Patent: Jun. 28, 2022

(54) ***BIDENS* PLANT NAMED 'FSK17S12'**

(50) Latin Name: *Bidens ferulifolia*
Varietal Denomination: 'FSK17S12'

(71) Applicant: Koichiro Nishikawa, Waddinxveen (NL)

(72) Inventor: Koichiro Nishikawa, Waddinxveen (NL)

( * ) Notice: Subject to any disclaimer, the term of this patent is extended or adjusted under 35 U.S.C. 154(b) by 0 days.

(21) Appl. No.: 17/574,627

(22) Filed: Jan. 13, 2022

(30) Foreign Application Priority Data

Jul. 21, 2021 (QZ) ..... PBR 2021/1905

(51) Int. Cl.
*A01H 6/14* (2018.01)
*A01H 5/02* (2018.01)

(52) U.S. Cl.
USPC ..... Plt./410

(58) Field of Classification Search
USPC ..... Plt./410
See application file for complete search history.

*Primary Examiner* — Annette H Para
(74) *Attorney, Agent, or Firm* — Penny J. Aguirre

(57) ABSTRACT

A new cultivar of *Bidens* plant named 'FSK17S12' that is characterized by its medium sized inflorescences, its inflorescences with ray floret colors that are bronze-yellow with yellow markings towards the base of the ray florets, its moderately vigorous plant habit, its moderately vigorous plant habit, and its mounding to semi-trailing plant habit.

2 Drawing Sheets

Botanical classification: *Bidens ferulifolia.*
Variety Denomination: 'FSK17S12'.

CROSS-REFERENCE TO A RELATED APPLICATION

This application claims priority to European Community Plant Variety Office (CPVO) Plant Breeder's Rights Application No. 2021/1905 filed on Jul. 21, 2021, under 35 U.S.C. 119(f), the entire contents of which is incorporated by reference herein. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Bidens ferulifolia* plant, botanically known as *Bidens ferulifolia* 'FSK17S12' and will be referred to hereinafter by its cultivar name, 'FSK17S12'. The new cultivar of *Bidens* is an evergreen perennial grown for landscape and container use.

The new cultivar was derived from a controlled breeding program conducted by the Inventor in Katsuta-Gun, Okayama-Pref., Nagi-chio Gyoho, Japan. The new cultivar arose from a cross made in October of 2013 between an unnamed and unpatented proprietary plants from the Inventor's breeding program; reference no. F1211 as the female parent and ref no. F1204 as the male parent. The Inventor selected 'FSK17S12' in October of 2014 as a single unique plant amongst the seedlings that resulted from the above cross.

Asexual propagation of the new cultivar was first accomplished by stem cuttings in March of 2015 by the Inventor in Katsuta-Gun, Okayama-Pref., Nagi-chio Gyoho, Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'FSK17S12' as a unique cultivar of *Bidens.*

1. 'FSK17S12' exhibits medium sized inflorescences.
2. 'FSK17S12' exhibits inflorescences with ray floret colors that are bronze-yellow with yellow markings towards the base of the ray florets.
3. 'FSK17S12' exhibits a moderately vigorous plant habit.
4. 'FSK17S12' exhibits a mounding to semi-trailing plant habit.

The female parent differs from 'FSK17S12' in having larger inflorescences with ray florets that are red in color with some yellow spots and a more mounding plant habit. The male parent differs from 'FSK17S12' in having inflorescences that are smaller in size, ray florets that are red in color with yellow hues, and a more vigorous growth habit. 'FSK17S12' can also be compared to the *Bidens* cultivar 'Golden Empire' (not patented). 'Golden Empire' differs from 'FSK17S12' in having a mounding to upright plant habit and inflorescences that are yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by Syngenta Flowers.

BRIEF DESCRIPTION OF THE DRAWINGS

The accompanying color photographs illustrate the overall appearance and distinct characteristics of the new *Bidens*. The photographs were taken of an 11-week-old plant of 'FSK17S12' as grown in a greenhouse in a 12-cm container in Andijk, The Netherlands.

The photograph in FIG. 1 provides a side view of the plant habit of 'FSK17S12' in bloom.

Figure 1:
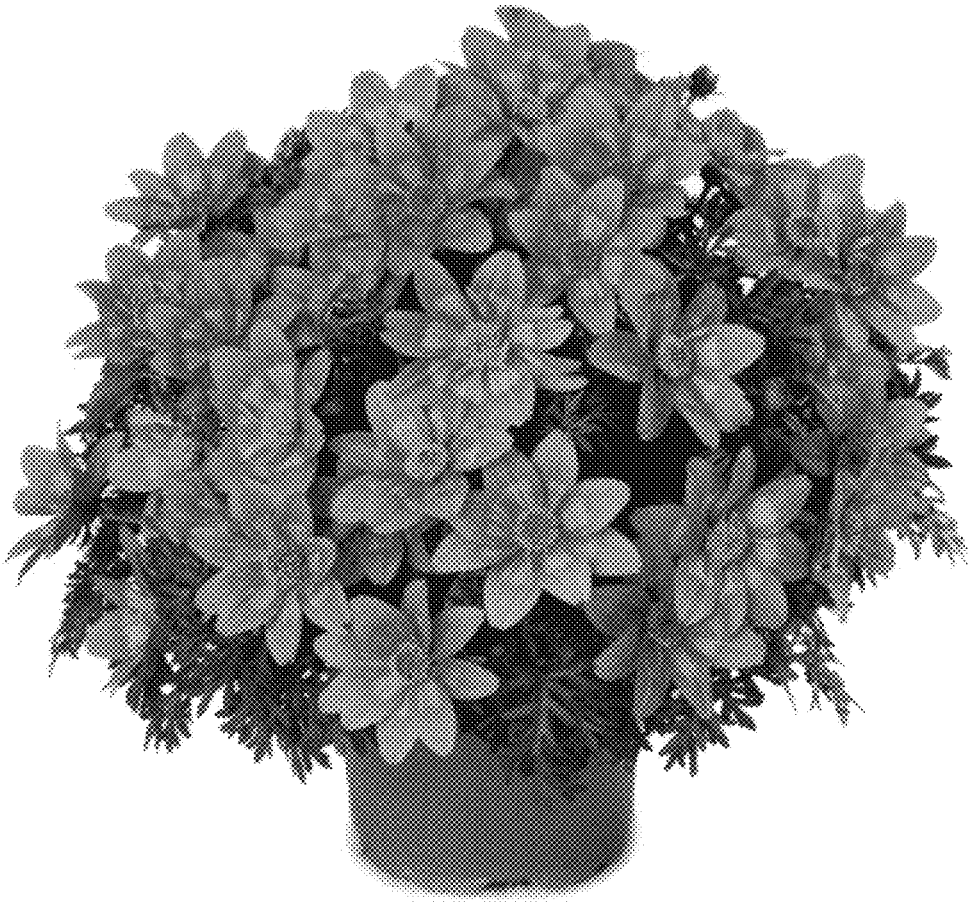
Figure 2:
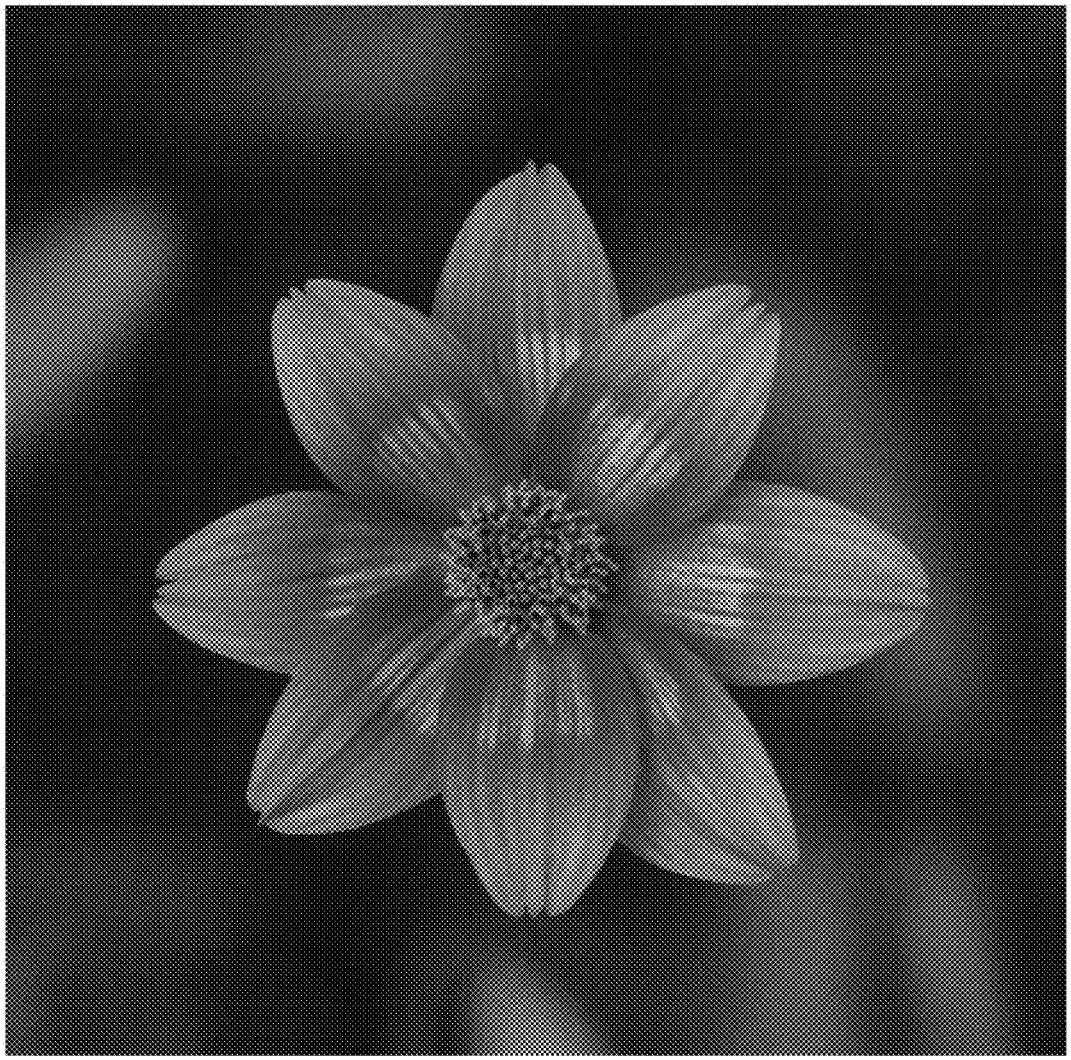

The photograph in FIG. 2 provides a close-up view of an inflorescence of 'FSK17S12'.

The colors in the photographs are as close as possible with the photographic and printing technology utilized and the color values cited in the detailed botanical description accurately describe the colors of the new *Bidens*.

DETAILED BOTANICAL DESCRIPTION

The following is a detailed description of 16-week-old plants of 'FSK17S12' as grown in 12-cm containers in a greenhouse in Andijk, The Netherlands. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period*.—Blooms continuously from spring through summer in Andijk, The Netherlands.

*Plant type*.—Evergreen perennial, grown as an annual.

*Plant habit*.—Mounding to semi-trailing.

*Height and spread*.—An average of 13 cm in height and 33 cm in width as a 16-week-old plant.

*Hardiness*.—At least to U.S.D.A Zones 9 to 11, grown as an annual.

*Diseases and pests*.—No susceptibility and resistance to pests and diseases has been observed.

*Root description*.—Fine, freely branching, 155B in color.

*Propagation*.—Stem cuttings.

*Root development*.—About 3 weeks to produce a rooted cutting and 8 weeks to produce a blooming plant from a rooted cutting.

*Growth rate*.—Moderately vigorous.

Stem description:

*Shape*.—Rounded, very slightly angled.

*Stem color*.—148A.

*Stem size*.—10 to 13 cm in length and 3 mm in diameter.

*Stem surface*.—Strongly pubescent with some anthocyanin presence.

*Stem strength*.—Strong.

*Internode length*.—1 to 2.5 cm.

*Branching habit*.—Freely branched, 6 to 8 stems per plant.

Foliage description:

*Leaf division*.—Simple.

*Leaf arrangement*.—Opposite.

*Leaf attachment*.—Petiolate.

*Leaf petioles*.—5 mm to 1.5 cm in length, 1.5 mm in diameter, 138B in color, surface slightly pubescent.

*Leaf shape*.—Ovate overall.

*Leaf margins*.—3-lobed, with lobe margins entire.

*Leaf margins*.—Entire.

*Leaf size*.—1.5 cm to 4 cm in length, 2 cm to 3.5 cm in width.

*Leaf base*.—Cuneate.

*Leaf apex*.—Acute.

*Leaf venation*.—Pinnate, 138A in color on upper and lower surface.

*Leaf surface*.—Upper and lower surface smooth.

*Leaf color*.—Young upper surface 138A, young lower surface 138B, mature upper surface N138A, mature lower surface N137A.

Flower description:

*Inflorescence type*.—Terminal and axillary capitulums, daisy-type.

*Lastingness of inflorescence*.—Average of 7 to 8 days, disc florets persistent, ray florets self-cleaning.

*Fragrance*.—Sweet, a bit spicy.

*Quantity of inflorescences*.—Free flowering, with an average of 60 open inflorescences and 10 buds per plant.

*Inflorescence size*.—An average of 8 mm in height and 4 cm in diameter.

*Inflorescence buds*.—Ovate in shape, an average of 1.2 cm in depth and 5 mm in diameter, pubescent surface, color; 147A, top 26A.

*Peduncle*.—Rounded in shape, strong, 4 cm in length and 2 mm in diameter, 147C in color, surface is densely pubescent covered with short soft hairs.

Involucral bracts:

*Involucral number*.—22.

*Involucral arrangement*.—Spirally placed around involucrum.

*Involucral size*.—4 mm to 6 mm in length, 1.5 mm to 2 mm in width.

*Involucral color*.—Upper and lower surface 147A.

*Involucral texture*.—Upper surface smooth, lower surface truncate.

*Involucral apex*.—Acute.

*Involucral base*.—Truncate.

*Involucral shape*.—Lanceolate.

Ray florets (no reproductive organs):

*Number*.—7 to 8.

*Shape*.—Ovate.

*Size*.—An average of 1.8 cm in length and 1 cm in width.

*Apex*.—Tridentate.

*Base*.—Cuneate.

*Margins*.—Entire.

*Surface*.—Both surfaces smooth.

*Color*.—When opening and fully open upper surface; N172A, base 17A, when opening and fully open lower surface; 26A with a hue of 17A, just before senescence; upper surface 22A, base 12A, lower surface 14A.

Disc Florets:

*Number*.—An average of 80.

*Shape*.—Tubular.

*Size*.—Average of 7 mm in length and 8 mm in width.

*Apex*.—Five-pointed.

*Margins*.—Entire.

*Surface*.—Both surfaces smooth.

*Color*.—Upper and lower surface when opening and fully open; 21A.

Reproductive organs:

*Presence*.—Disc florets only.

*Gynoecium*.—1 Pistil, an average of 4 mm in length, stigma; decurrent, 14A in color, style; 2.5 mm in length, ovary; 145D in color.

*Androecium*.—5 stamens, anther; basifixed, linear, 1 mm to 1.5 mm in length, 200A in color, filament; 1 cm in length, pollen; moderate, 17A in color.

*Seed*.—No seed development has been observed to date.

It is claimed:

1. A new and distinct cultivar of *Bidens* plant named 'FSK17S12' as herein illustrated and described.

* * * * *